United States Patent [19]

Shoesmith, deceased

[11] Patent Number: Plant 5,886

[45] Date of Patent: Feb. 17, 1987

[54] CHRYSANTHEMUM PLANT NAMED CINNAMON

[75] Inventor: Leonard H. Shoesmith, deceased, late of Westfield, England, by May Victoria Shoesmith, executrix

[73] Assignee: Ball Pan Am Plant Co., Parrish, Fla.

[21] Appl. No.: 712,696

[22] Filed: Mar. 18, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Cinnamon having a dwarf habit, flat capitulum form and single capitulum type, bronze flower color, eight week response, and ability to be grown in 9 cm. pots year around.

1 Drawing Figure

1

The present invention comprises a new and distinct cultivar of *Chrysanthemum morifolium,* Ramat., hereinafter referred to by the cultivar named Cinnamon.

Cinnamon is a product of a planned breeding program which had the objective of creating new chrysanthemum cultivars with eight an (8) week response, bronze daisy type flowers, and a dwarf habit for year around growing in 9 cm. pots. Such traits in combination were not present in previously available commercial cultivars.

Cinnamon was originated from a hybridization made by Leonard H. Shoesmith in a controlled breeding program in Westfield, Woking, England in 1976. The male and female parents are unknown at this time. Cinnamon was discovered and selected as one flowering plant within the progeny of the parentage by applicant in November, 1977 in a controlled environment in West Chicago, Ill., and given the code name FG7-19-BS.

The first act of asexual reproduction of Cinnamon was accomplished when vegetative cuttings were taken from the initial selection in February, 1978 in a controlled environment in West Chicago, Ill. by a technician working under formulations established and supervised by Leonard H. Shoesmith. Horticultural examination of selected units initiated in March, 1978 has demonstrated that the combination of characteristics as herein disclosed for Cinnamon are firmly fixed and are retained through successive generations of asexual reproduction.

Cinnamon has not been observed under all possible environmental conditions. The phenotype may vary signficantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Cinnamon, which in combination distinguish this chrysanthemum as a new and distinct cultivar:

1. Flat capitulum form.
2. Single capitulum type.
3. Bronze flower color.
4. Dwarf habit extending 10–15 cm. upwardly from edge of pot.
5. Eight (8) week response.
6. Ability to be grown in a 9 cm. pots year around in most areas, requiring little B-9 treatment.

2

Of the many commercial cultivars known to the present inventor, the most similar in comparison to Cinnamon is Cirbronze, disclosed in U.S. Plant Pat. No. 4,292. In comparison to Cirbronze, Cinnamon has flatter ray florets, is shorter and more suitable for 9 cm. pots, and is one week earlier in response. The flower type, form, and color of Cinnamon are similar to those same characteristics of Cirbronze.

The accompanying photographic drawing shows typical inflorescense characteristics of Cinnamon, with colors being as nearly true as possible with illustrations of this type.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—*Chrysanthemum morifolium,* Ramat., CV Cinnamon.

*Commercial.*—Daisy spray, four (4) inch.

I. Inflorescence:

A. *Capitulum.*—Form: Flat. Type: Daisy. Diameter Across Face: 3–5 cm.

B. *Corolla of ray florets.*—Color (General Tonality From a Distance of Three Meters): Reddish Bronze. Color (Under Surface): 167 B. Color (Top Surface): 169 A.

C. *Corolla of disc florets.*—Color (Mature): Yellow. Color (Immature): Yellow.

D. *Reproductive organs.*—Androecium: Present in disc florets only; numerous. Gynoecium: Present in both ray and disc florets; numerous.

II. Plant:

A. *General appearance.*—Height: 10–15 cm. above edge of pot when properly grown.

B. *Foliage.*—Color (Under Surface): 147 B. Color (Top Surface): 147 A. Shape: Ovate and deeply lobed.

I claim:

1. A new and distinct cultivar of Chrysanthemum named Cinnamon, as described and illustrated, and particularly characterized by its dwarf habit; flat capitulum form and single capitulum type; bronze flower color; eight week response, and by its ability to be grown in 9 cm. pots year around.

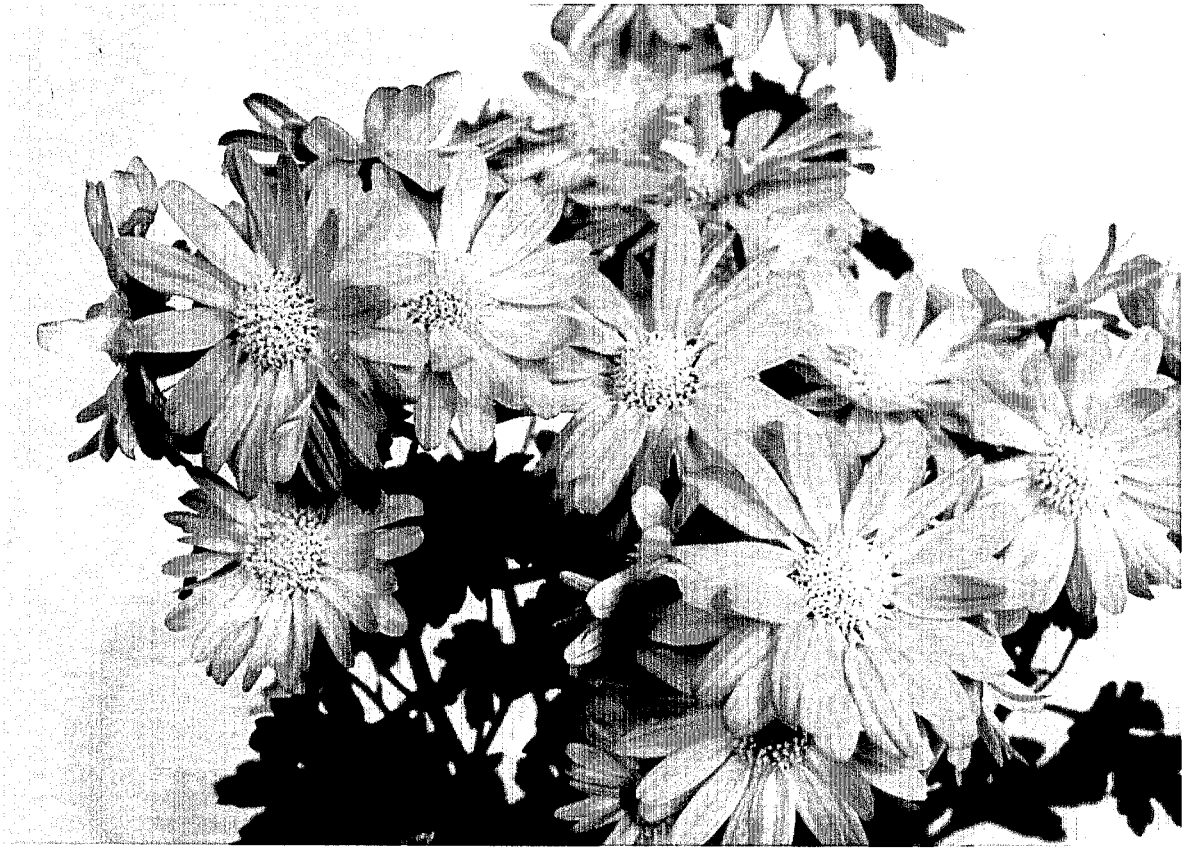

* * * * *